United States Patent [19]
Yoshida

[11] 4,054,995
[45] Oct. 25, 1977

[54] PIN WITH SLEEVE FOR MAKING DENTAL PROSTHESIS

[76] Inventor: Harry Y. Yoshida, 5267 Eileen Drive, San Jose, Calif. 95129

[21] Appl. No.: 682,202

[22] Filed: May 3, 1976

[51] Int. Cl.² .............................................. A61C 13/00
[52] U.S. Cl. ......................................................... 32/11
[58] Field of Search .................................. 32/11, 40 R

[56] References Cited
U.S. PATENT DOCUMENTS 3,226,827  1/1966  Spalten ...................................... 32/11

Primary Examiner—Robert Peshock
Attorney, Agent, or Firm—Jack M. Wiseman

[57] ABSTRACT

In the making of fixed dental prosthesis, a model is employed, which is an accurate replica of the patient's teeth and gums. For reinforcement, the model is fixed to a base. A model comprises a replica of teeth remaining in the patient's mouth and a replica of teeth to be prepared by restorative dentistry. For preparing the teeth by restorative dental techniques, a die is used. It is desired that the die be removed from and replaced in the model with facility, the die be returned to the model in a precise manner, the die be removable from the base on which the model is secured, and the die be prevented from rotating relative to the pin. Toward this end, the pin of the present invention is formed with a tip that is embedded in the extremity of the die facing the model for fixing the die thereto. The tip has a side elevation contour somewhat similar either to a triangular configuration or a rectangular configuration. Extending from the tip is a shank having one portion extending beyond another portion thereof. The longer portion of the shank is received by a bore formed in a rubber sleeve, which is disposed in the base to which the model is fixed. A wall of the sleeve is planar with the wall of the base removed from the model. The shorter portion of the shank at the extremity thereof abuts against the wall of the rubber sleeve confronting the die.

25 Claims, 7 Drawing Figures

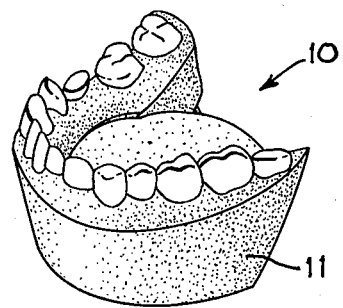
Fig_1
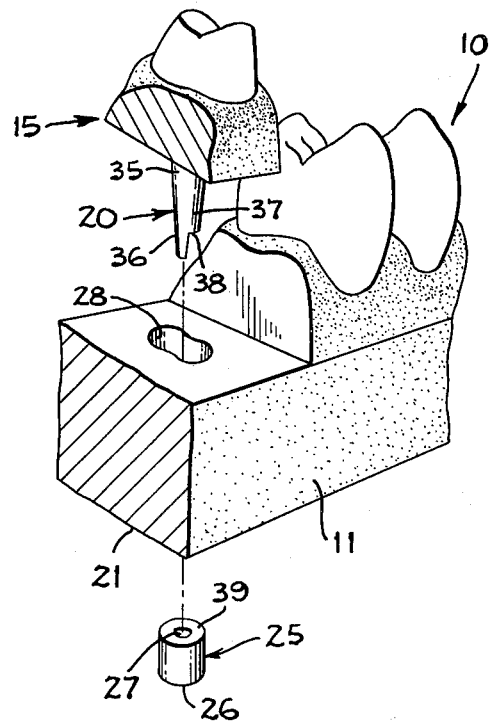
Fig_2
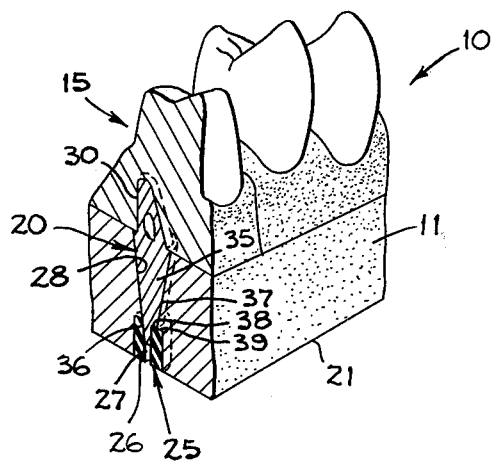
Fig_3
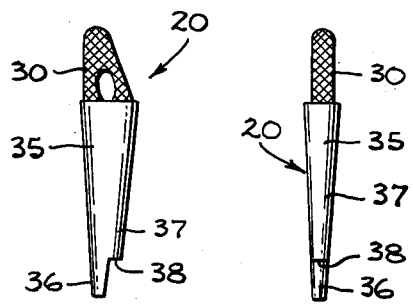
Fig_4    Fig_5
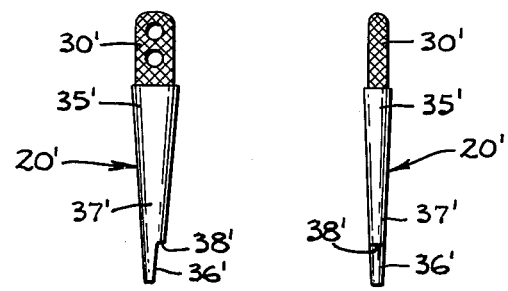
Fig_6    Fig_7

PIN WITH SLEEVE FOR MAKING DENTAL PROSTHESIS

BACKGROUND OF THE INVENTION

The present invention relates in general to models employed in restorative or prosthetic dentistry, and more particularly to a pin fixed in a removable die of a model and received by a base to which the model is received.

In the making of a fixed dental prosthesis (i.e. gold and ceramic crown or bridge) it is required that an accurate replica of the existing teeth and gums (dentition) be made. The replicas, herein referred to as models, are made by taking an impression of dentition. Material capable of adapting to the exact shape and dimension of the dentition are, for example, silicon, rubber and agar hydrocolloid. The impression is a "negative" model in which plaster, such as calcium sulfatehemihydrate, is poured. Upon removal from the impression, the plaster forms the model on which the prosthesis is constructed. The model is secured to a base of the plaster to increase its overall strength.

The plaster model comprises teeth which are replicas of the teeth remaining in the mouth of the patient and a replica of the teeth to be prepared by prosthetic or restorative dentistry. It is the teeth prepared for the prosthesis to be developed by restorative dentistry that requires a pin.

The replica of the teeth to be prepared by prosthetic or restorative dentistry is known as a die. It is desired in restorative dentistry that the die be removable and replaceable in the model. The die should be returned to the model in an exact position. Additionally, the die should not be susceptible to rotation about the pin. During fabrication of the prosthesis, the pin should be able to withstand torque stresses applied to the die. Should the tip of the pin fracture because of torque stresses, then the pin should be able to be repaired and restored with facility and ease of operation.

Additionally, the pin should be constructed to obviate the need for depressions in the wall of the die confronting the model. Furthermore, the tip of the pin should be constructed to fit into the narrow lower mouth anterior teeth depression (labiel-lingual). The opening in the base formed to receive the pin should be able to be cleaned with facility and ease of operation should debris, foreign matter, burrs or stones be deposited therein. Debris and foreign matter in the opening of the base detracts from the accurate seating of the shank of the pin in the opening of the base during the replacement of the die in the model.

Heretofore, dowel pins have been employed for indexing a removable die of a model. Such dowel pins have generally been made of brass. The dowel pins were fixed in the die and extended therefrom to be received by a suitable opening in the base. The dowel pins serve to index and locate the die relative to the model. Typically, the dowel pin had a cylindrical configuration or a surface equidistance from the axis of the pin. At times, a portion of the cylindrical surface would have a flat taper portion extending in the axial direction equidistance from the axis thereof.

Customarily, the dowel pin had a knurled end for retention in the die. In some instances, an adhesive, such as cyano acrylate ester, on a smooth surface was employed to secure the dowel pin in the die. At other times, the dowel pin had a stem with flat sides for retention in the die.

Additionally, the dies heretofore employed had two dowel pins extending from the die. Some dowel pins used sleeves for improved accuracy in indexing the die in the model. The sleeve may have facilitated the removal of the die from the model.

In the patent to Lystager U.S. Pat. No. 3,704,519, issued on Dec. 5, 1972, for Method To Prepare A Dental Model, there is disclosed a die with a pair of spaced pins embedded therein. Bushings are disposed in the base for receiving the pins. The patent to Cooper U.S. Pat. No. 3,286,350, issued Nov. 22, 1966, for Dowel And Clip Assembly And Its Use In The Manufacture Of Dental Restorations discloses a pin embedded in a die that is received by a rubber core embedded in the base. The shank of the pin is undercut to rest on the top wall of a spring clip, which is also embedded in the base. As for the patent to Spalten U.S. Pat. No. 3,226,827, issued on Jan. 4, 1966, for Dental Apparatus, there is shown a dowel pin with a tip having flat walls. The patent to Weissman U.S. Pat. No. 3,153,283 and the patent to Susman et al. U.S. Pat. No. 3,518,761, disclose pins received by sleeves.

The patent to Bailey U.S. Pat. No. 1,867,300, issued on July 12, 1932, for Metallic Socket And Mold For Amalgam Dies shows a socket receiving the shank of a die, while the patent to Spalten et al. U.S. Pat. No. 2,851,728, issued on Sept. 16, 1958, for Interlockable Dental Pin And Repositioning Gauge And Method Of Using discloses a stem for a pin having trapezoidal cross-sectional areas. Another patent of interest is the patent to Waltke U.S. Pat. No. 3,453,736, issued on July 8, 1969, for Dowels For Fireable Ceramic Dies And Method For Their Use, which shows dowels of various configurations. Another patent of interest is the patent to Stengel U.S. Pat. No. 3,478,428, issued on Nov. 18, 1969, for Apparatus For Dental Models.

SUMMARY OF THE INVENTION

A pin for a die removably mounted in a model in prosthetic or restorative dentistry in which the pin includes a stem embedded in the portion of the die confronting the model for fixing the die thereto. Extending from the stem is a shank having one portion thereof longer than another portion thereof. The model is fixed to a base. Embedded in the base is a sleeve. The free end of the longer portion of the shank is received by the bore of the sleeve and the free end of the shorter portion of the shank abuts against the confronting wall of the sleeve.

By virtue of the sleeve, which in the preferred embodiment is rubber, the shorter portion of the shank of the pin engages the confronting wall thereof as a stop. In this manner, the length of the pin exposure is controlled and an operator senses when he has reached a controlled distance by the engagement with relatively soft material. The soft material of the sleeve avoids the need of reshaping the free end of the shank of the pin. The removing of burrs and stones that previously accumulated on the shank or free end of the shank of the pin is no longer necessary.

Heretofore, depressions were formed in the confronting surfaces of the die and model to inhibit rotation of the die. Through the pin and the rubber sleeve of the present invention, the need for the depressions in the confronting walls of the die and model has been obviated.

The employment of the rubber sleeve enables the opening formed in the base to receive the free end of the shank of the pin to be cleaned with facility and ease of operation. Debris, foreign matter, stones and burrs which have a tendency to accumulate in the opening can be easily removed.

A feature of the present invention is the stem or tip of the pin which has either a triangular contour or a rectangular shape in the side elevation. The tip or stem of the pin serves to reduce torque stress and, should it fracture, it is easy to repair or restore. The tip or stem of the pin fits into the narrow lower mouth anterior teeth impression (labiel-lingual).

DESCRIPTION OF THE DRAWINGS

FIG. 1 is a perspective view of a model used in prosthetic or restorative dentistry secured to a base.

FIG. 2 is a fragmentary perspective view of the model shown in FIG. 1 with a die thereof removed from the model.

FIG. 3 is a fragmentary perspective view of the model shown in FIG. 1 to illustrate the pin of the present invention received by the sleeve of the present invention that is embedded in the base on which the model is secured.

FIG. 4 is a side elevation view of the pin embodying the present invention with a stem or tip having a triangular configuration.

FIG. 5 is an end elevation view of the pin shown in FIG. 4.

FIG. 6 is a side elevation view of a modification of the pin shown in FIGS. 4 and 5 having a rectangular configuration.

FIG. 7 is an end elevation view of the pin shown in FIG. 6.

DESCRIPTION OF THE PREFERRED EMBODIMENTS

In prosthetic or restorative dentistry, a fixed dental prosthesis is fabricated, which may be gold or ceramic crown or bridge. This procedure requires an accurate replica of the existing teeth and gums. The existing teeth and gums are called dentition and the replica is called a model. Initially, an impression is made of the dentitions. Materials commonly employed for taking the impression is silicon rubber or agar hydrocolloid. The impression is a "negative" model in which plaster is poured. Commonly employed plaster for this purpose is a calcium sulfatehemihydrate. Upon removal from the impression, the plaster forms a model on which the prosthesis is constructed.

Illustrated in FIG. 1 is a model 10, which is secured to a base 11 for improved overall strength. The base 11 is generally made of the same material as is the model 10 and the model 10 is fixed to the base 11 in a well-known manner by adhesion. The plaster model comprises replica of teeth remaining in the patient's mouth and a replica of teeth to be prepared by restorative or prosthetic dentistry.

It is the replica of teeth from which a prosthetic restoration is prepared that employs the present invention. The portion of the model 10 from which the prosthesis is to be developed on or fabricated from is a die 15 (FIGS. 2 and 3). The die 15 is generally formed of the same material as is the model, namely: a plaster of calcium sulfatehemihydrate.

In order to use the die 15 for prosthetic restoration, the die 15 must be removable from the model 10 and must be replaced in the model 10 (FIGS. 2 and 3). As previously described, an impression of the patient's mouth is the first made in the usual manner. Thereafter, the model 10 is cast from the impression and, when a slurry of plaster material has been fully poured, a pin 20 is inserted into the plaster adjacent to the tooth recess or cavity before the plaster material has been fully hardened or cured. The pin 20 is inserted so that its orientation is generally perpendicular to the plane of occlusion.

After the plaster has fully hardened with the pin 20 therein, a separator medium, such as "Vaseline", is placed on the wall of the die 15 to confront the base 11 to be formed. Thereupon, additional plaster material is poured thereover up to a predetermined level to form the base 11. A wall 21 of the base 11 faces in a direction away from the die 15. When the plaster material for the base 11 is fully poured, a rubber or plastic sleeve 25 is inserted into the plaster forming the base 11 with its orientation generally perpendicular to the plane of occlusion. A wall 26 of the sleeve 25, in the exemplary embodiment, is planar with the wall 21 of the base 11. A bore 27 is formed in the sleeve 25 for receiving the free end of the pin 20.

At this time, the base 11 and the model 10 are fully hardened and cured. To remove the die 15 from the model 10, the model 10 is cut by a saw or the like along the sides of the die 15. The lower wall of the die 15 is separable through the separator medium. The pin is preferably made of a suitable material, such as brass. The free end of the pin 20 is received by the sleeve 25 and the opening 28 formed in the base 11, while the base 11 is formed.

According to the present invention, the pin 20 comprises a tip or stem 30. The top wall thereof is arcuate to conform to the drilling end of a burr or the like. In the exemplary embodiment, the stem 30 is knurled and has a side elevation contour substantially in the form of a triangle. The side and end walls thereof are flat to reduce torque stress. Openings are formed in the side walls for receiving various tools. During the fabrication of the prosthesis, the pin 20 is subjected to torque stresses, which are applied to the die 15. Thus, the stem 30 is constructed to reduce torque stress and is easily replaced or restored when broken or damaged by torque stresses. Additionally, the stem 30 is arranged to fit into the narrow lower mouth anterior teeth impression (labiel-lingual).

Extending from the stem 30 is a shank 35 of the pin 20, which is tapered to decrease in depth as the shank extends from the stem 30. The stem 30 is of lesser cross-sectional area than the portion of the shank 35 adjoined thereto to define a shoulder or flange surrounding the tip 30 for abutment with the confronting wall of the die 15. The shank 35 has a longer portion 36 and a shorter portion 37. The free end of the shorter portion 37 defines a shoulder 38 in cooperation with the longer portion 36. The longer portion 36 and the shorter portion 37 may be formed from two shanks integrated into a single shank by being in continuous relation or may be formed from a unitary structure to define, in the preferred embodiment, a cross-sectional area of oval, square, triangular, or rectangular configuration. Even when two shanks are united, the resulting shank will have a configuration to enable the shank 35 to have a precise location relative the opening 28 formed in the base 11. In this manner, the die 15 will be accurately seated in the model 10 and have a precise location for each replacement in the model 10.

The longer portion 36 of the shank 35 is received by the bore 27 of the sleeve 25 and the shoulder 38 of the shank 35 will seat on a wall 39 of the sleeve 25, which surrounds the bore 27 and which is parallel to the wall 26 of the sleeve 25. Thus, the sleeve 25 serves as a stop to control the length of the pin 20 embedded in the die 15 during the initial fabrication of the model 10. By virtue of this arrangement, the opening 28 in the base 11 can be cleaned with facility to remove burrs, stones and debris which may accumulate therein. Additionally, the free end of the shank 35 does not require reshaping or the removal of burrs and stones. With the sleeve 25 made of rubber, the free ends of the shank 35 engage a relatively soft material.

In the modification of the pin 20 shown in FIGS. 6 and 7, the stem or tip 30' of the pine 20' thereof has a substantially rectangular configuration when viewed in side elevation. The tip 30' is knurled. The top wall thereof is arcuate to conform to the contour of the drilling end of a burr or the like. Openings are formed in the flat side walls for receiving suitable tools. All other parts of the pin 20' are similar to that previously described for the pin 20 and, hence, have been designated with the same reference numeral with the addition of a prime. The tip 30' is of lesser cross-sectional area than the portion of the shank 35' adjoined thereto to define a shoulder or flange surrounding the tip 30' for abutment with the confronting wall of the die 15.

I claim:
1. A dental prosthesis comprising:
   a. a model;
   b. a die removably positioned in said model;
   c. a pin comprising:
      1. a stem embedded in said die; and
      2. a shank extending from said stem and projecting out of said die, said shank having a longer portion and a shorter portion defining a shoulder and a tip at the lower extremity of said shank;
   d. a base supporting said model, said base being formed with a first wall confronting said die against which said die is disposed, said base being formed with an opening to receive said longer and shorter portions of said shank of said pin; and
   e. a sleeve disposed in said base, said sleeve being formed with a bore therethrough aligned with said opening in said base in which to dispose the tip of the longer portion of said shank of said pin to provide a receptacle for the tip of said shank, said sleeve being formed with a first wall confronting said die and surrounding said bore against which said shoulder of said shank of said pin abuts to limit the extent of the insertion of said shank into said base said sleeve extending only along entire length of said tip.
2. The dental prosthesis as claimed in claim 1 wherein said sleeve is made of a softer material than the material from which said base is made to enable an operator to sense the reaching of a controlled distance for the insertion of said shank into said base and to provide a receptacle for the tip of said shank which is less abrasive to the tip of said shank.
3. The combination of a pin and sleeve for removably positioning a die in a model secured to a base for dental prosthesis comprising:
   a. said pin comprising:
      1. a stem adapted to be embedded in the die, and
      2. a shank extending from said stem and adapted for projecting out of said die, said shank having a longer portion and a shorter portion defining a shoulder in a tip at the lower extremity of said shank; and
   b. a sleeve adapted to be disposed in said base, said sleeve being formed with a bore therethrough in which to dispose the tip of the longer portion of said shank of said pin to provide a receptacle for the tip of said shank, said sleeve being formed with a wall surrounding said bore against which said shoulder of said shank of said pin abuts said sleeve extending only along entire length of said tip.
4. The combination as claimed in claim 3 wherein said sleeve is made of a plastic material.
5. The combination as claimed in claim 3 wherein said sleeve is made of rubber material.
6. The combination as claimed in claim 3 wherein said stem is formed with flat side walls.
7. The combination as claimed in claim 3 wherein said stem has substantially a trianguloid configuration.
8. The combination as claimed in claim 3 wherein said stem has substantially a rectanguloid configuration.
9. The combination as claimed in claim 7 wherein said sleeve is made of plastic material.
10. The combination as claimed in claim 8 wherein said sleeve is made of plastic material.
11. The combination as claimed in claim 7 wherein said sleeve is made of rubber.
12. The combination as claimed in claim 8 wherein said sleeve is made of rubber.
13. The dental prosthesis as claimed in claim 2 wherein said sleeve is formed with a second wall substantially parallel with said first wall of said sleeve, and wherein said base is formed with a second wall substantially parallel with said first wall of said base, said second wall of said sleeve being disposed substantially in planar relation with said second wall of said base to facilitate the removal of foreign matter accumulating in the opening of said base.
14. the dental prosthesis as claimed in claim 2 wherein said sleeve is made of a plastic material.
15. A dental prosthesis as claimed in claim 2 wherein said sleeve is made of a rubber material.
16. A dental prosthesis as claimed in claim 13 wherein said sleeve is made of plastic material.
17. A dental prosthesis as claimed in claim 13 wherein said sleeve is made of rubber material.
18. A dental prosthesis as claimed in claim 14 wherein said stem is formed with flat side walls.
19. A dental prosthesis as claimed in claim 18 wherein said stem has substantially a trianguloid configuration.
20. A dental prosthesis as claimed in claim 18 wherein said stem has substantially a rectanguloid configuration.
21. A dental prosthesis as claimed in claim 15 wherein said stem is formed with flat side walls.
22. A dental prosthesis as claimed in claim 21 wherein said stem has substantially a trianguloid configuration.
23. A dental prosthesis as claimed in claim 21 wherein said stem has substantially a rectanguloid configuration.
24. The combination as claimed in claim 3 wherein said sleeve is made of a soft plastic material.
25. The combination as claimed in claim 3 wherein said sleeve is made of a soft rubber material.

* * * * *